United States Patent
Lazzara et al.

(10) Patent No.: US 8,221,499 B2
(45) Date of Patent: Jul. 17, 2012

(54) INFECTION-BLOCKING DENTAL IMPLANT

(75) Inventors: Richard J. Lazzara, Lake Worth, FL (US); Thomas S. Heylmun, Meriden, CT (US); Keith D. Beaty, Jupiter, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 1444 days.

(21) Appl. No.: 09/237,605

(22) Filed: Jan. 25, 1999

(65) Prior Publication Data

US 2001/0004711 A1    Jun. 21, 2001

Related U.S. Application Data

(63) Continuation of application No. 08/778,503, filed on Jan. 3, 1997, now Pat. No. 5,863,201, which is a continuation-in-part of application No. 08/607,903, filed on Feb. 27, 1996, now Pat. No. 5,876,453, which is a continuation-in-part of application No. 08/351,214, filed on Nov. 30, 1994, now abandoned.

(60) Provisional application No. 60/009,592, filed on Jan. 4, 1996.

(51) Int. Cl.
*A61F 2/28* (2006.01)

(52) U.S. Cl. ............. 623/16.11; 623/23.5; 433/173; 433/201.1

(58) Field of Classification Search ............. 623/16, 623/23.5, 23.53, 23.55, 23.76, 16.11; 433/173, 433/199.1, 201.1
See application file for complete search history.

(56) References Cited

U.S. PATENT DOCUMENTS

| | | | |
|---|---|---|---|
| 3,022,783 A | 2/1962 | Tucker, Jr. | |
| 3,605,123 A | 9/1971 | Hahn | |
| 3,767,437 A | 10/1973 | Cruz, Jr. | |
| 3,790,507 A | 2/1974 | Hodosh | 433/173 |
| 3,855,638 A | 12/1974 | Pilliar | 3/1 |
| 3,919,723 A | 11/1975 | Heimke et al. | |
| 3,986,212 A | 10/1976 | Sauer | |
| 3,987,499 A | 10/1976 | Scharbach et al. | |
| 4,011,602 A | 3/1977 | Rybicki et al. | 3/1.9 |
| 4,051,598 A | 10/1977 | Sneer | |
| 4,145,764 A | 3/1979 | Suzuki et al. | 3/1.9 |
| 4,146,936 A | 4/1979 | Aoyagi et al. | |
| 4,180,910 A | 1/1980 | Straumann et al. | |
| 4,195,409 A | 4/1980 | Child | 433/175 |
| 4,199,864 A | 4/1980 | Ashman | |

(Continued)

FOREIGN PATENT DOCUMENTS

AT    328 067    5/1975

(Continued)

OTHER PUBLICATIONS

ASTM Designation F 86-84, "*Standard Practice for Surface Preparation and Marking of Metallic Surgical Implants*".

(Continued)

*Primary Examiner* — Paul Prebilic
(74) *Attorney, Agent, or Firm* — Nixon Peabody LLP (57) ABSTRACT

An infection-blocking dental implant in which a threaded portion which contacts bone is roughened except for up to three threads which may be exposed by bone recession after implantation, which have a smooth surface. Preferably, the implant is of titanium or titanium alloy and the threaded portion is roughened by a two-step acid treatment.

16 Claims, 6 Drawing Sheets

U.S. PATENT DOCUMENTS

| | | |
|---|---|---|
| 4,223,412 A | 9/1980 | Aoyagi et al. |
| 4,261,350 A | 4/1981 | Branemark et al. |
| 4,330,891 A | 5/1982 | Branemark et al. |
| 4,336,618 A | 6/1982 | Raab |
| 4,366,183 A | 12/1982 | Ghommidh et al. |
| 4,406,761 A | 9/1983 | Shimogori et al. |
| 4,530,116 A | 7/1985 | Frey ............................... 623/23 |
| 4,547,157 A | 10/1985 | Driskell ....................... 433/173 |
| 4,547,327 A | 10/1985 | Bruins et al. ..................... 264/16 |
| 4,608,052 A * | 8/1986 | Van Kampen et al. ......... 623/22 |
| 4,629,464 A | 12/1986 | Takata et al. |
| 4,654,314 A | 3/1987 | Takagi et al. ................... 501/82 |
| 4,687,675 A | 8/1987 | Nakano et al. |
| 4,693,986 A | 9/1987 | Vit et al. |
| 4,702,930 A | 10/1987 | Heide et al. |
| 4,704,126 A | 11/1987 | Baswell et al. ................. 623/10 |
| 4,722,688 A | 2/1988 | Lonca ........................... 433/173 |
| 4,746,532 A | 5/1988 | Suzuki et al. ..................... 427/2 |
| 4,818,559 A | 4/1989 | Hama et al. ...................... 427/2 |
| 4,826,434 A * | 5/1989 | Krueger ....................... 433/174 |
| 4,839,215 A | 6/1989 | Starling |
| 4,861,733 A | 8/1989 | White |
| 4,865,603 A | 9/1989 | Noiles ............................. 623/18 |
| 4,871,578 A | 10/1989 | Adam et al. |
| 4,874,434 A | 10/1989 | Riggs, Jr. .......................... 134/3 |
| 4,878,914 A | 11/1989 | Miwa et al. ..................... 623/16 |
| 4,882,196 A | 11/1989 | Shimamune et al. |
| 4,908,030 A | 3/1990 | Linkow et al. .................. 623/16 |
| 4,911,953 A | 3/1990 | Hosonuma et al. ........... 427/224 |
| 4,919,751 A | 4/1990 | Sumita et al. |
| 4,932,868 A | 6/1990 | Linkow et al. |
| 4,938,938 A | 7/1990 | Ewers et al. |
| 4,944,754 A | 7/1990 | Linkow et al. .................. 623/16 |
| 4,960,646 A | 10/1990 | Shimamune et al. |
| 4,963,145 A | 10/1990 | Takagi et al. |
| 4,969,906 A | 11/1990 | Kronman ........................ 623/16 |
| 4,988,299 A | 1/1991 | Branemark ................... 433/174 |
| 5,000,685 A | 3/1991 | Brajnovic ..................... 433/173 |
| 5,030,096 A | 7/1991 | Hurson et al. ................ 433/173 |
| 5,032,552 A | 7/1991 | Nonami et al. |
| 5,034,352 A | 7/1991 | Vit et al. |
| 5,039,546 A | 8/1991 | Chung et al. |
| 5,071,351 A | 12/1991 | Green et al. .................... 422/23 |
| 5,108,399 A | 4/1992 | Eitenmuller et al. |
| 5,141,576 A | 8/1992 | Shimamune et al. |
| 5,180,564 A | 1/1993 | Wahl et al. |
| 5,188,800 A | 2/1993 | Green et al. .................. 433/173 |
| 5,190,795 A | 3/1993 | Culler ........................... 427/226 |
| 5,195,891 A | 3/1993 | Sulc |
| 5,199,873 A | 4/1993 | Schulte et al. ................ 433/174 |
| 5,205,745 A | 4/1993 | Kamiya |
| 5,205,921 A | 4/1993 | Shirkanzadeh |
| 5,219,361 A | 6/1993 | von Recum et al. |
| 5,222,983 A | 6/1993 | Schmitz et al. ................. 623/16 |
| 5,242,706 A | 9/1993 | Cotell et al. |
| 5,258,030 A | 11/1993 | Wolfarth et al. ............... 623/16 |
| 5,263,986 A | 11/1993 | Noiles et al. .................... 623/22 |
| 5,279,831 A | 1/1994 | Constantz et al. |
| 5,297,963 A | 3/1994 | Dafatry ......................... 433/172 |
| 5,306,305 A | 4/1994 | Lee |
| 5,310,464 A | 5/1994 | Redepenning |
| 5,316,476 A | 5/1994 | Krauser ........................ 433/173 |
| 5,316,477 A | 5/1994 | Calderon ...................... 433/173 |
| 5,324,199 A | 6/1994 | Branemark |
| 5,344,425 A | 9/1994 | Sawyer .......................... 606/198 |
| 5,344,457 A | 9/1994 | Pilliar et al. .................... 623/16 |
| 5,360,448 A | 11/1994 | Thramann ....................... 623/18 |
| 5,362,237 A | 11/1994 | Chalifoux ..................... 433/220 |
| 5,366,374 A | 11/1994 | Vlassis .......................... 433/165 |
| 5,368,480 A | 11/1994 | Balfour et al. ................ 433/141 |
| 5,368,483 A | 11/1994 | Sutter et al. ................... 433/173 |
| 5,399,090 A | 3/1995 | Padros-Fradera ............ 433/173 |
| 5,405,436 A | 4/1995 | Maurer et al. |
| 5,427,754 A | 6/1995 | Nagata et al. |
| 5,433,606 A | 7/1995 | Niznick et al. ................ 433/173 |
| 5,441,536 A | 8/1995 | Aoki et al. |
| 5,456,723 A | 10/1995 | Steinemann et al. .......... 623/16 |
| 5,472,734 A | 12/1995 | Perrotta et al. |
| 5,478,237 A | 12/1995 | Ishizasawa ................. 433/201.1 |
| 5,484,286 A | 1/1996 | Hansson ..................... 433/201.1 |
| 5,489,210 A | 2/1996 | Hanosh .......................... 433/173 |
| 5,496,399 A | 3/1996 | Ison et al. |
| 5,503,558 A | 4/1996 | Clokie .......................... 433/173 |
| 5,543,019 A | 8/1996 | Lee et al. |
| 5,564,923 A | 10/1996 | Grassi et al. ................. 433/173 |
| 5,571,017 A | 11/1996 | Niznick ....................... 433/174 |
| 5,571,188 A | 11/1996 | Ellingsen et al. |
| 5,573,401 A | 11/1996 | Davidson et al. .......... 433/201.1 |
| 5,588,838 A | 12/1996 | Hansson et al. .............. 433/173 |
| 5,591,029 A | 1/1997 | Zuest |
| 5,603,338 A | 2/1997 | Beaty .............................. 623/16 |
| 5,607,480 A | 3/1997 | Beaty .............................. 623/16 |
| 5,639,237 A | 6/1997 | Fontenot |
| 5,816,811 A | 10/1998 | Beaty .......................... 433/173 |
| 5,863,201 A | 1/1999 | Lazzara et al. ............ 433/201.1 |
| 5,876,453 A | 3/1999 | Beaty .............................. 623/16 |
| 5,989,027 A * | 11/1999 | Wagner et al. ............... 433/173 |
| 6,069,295 A * | 5/2000 | Leitao ............................ 623/11 |
| 6,491,723 B1 | 12/2002 | Beaty |
| 6,652,765 B1 | 11/2003 | Beaty |
| 7,048,870 B1 * | 5/2006 | Ellingsen et al. ............. 216/109 |

FOREIGN PATENT DOCUMENTS

| | | | |
|---|---|---|---|
| CA | 926552 | 5/1973 | |
| DE | 2 313 678 | 10/1974 | |
| DE | 27 17 615 A1 | 10/1978 | |
| EP | 202 031 A2 | 11/1986 | |
| EP | 212 929 A2 | 3/1987 | |
| EP | 0 213 836 | 11/1987 | |
| EP | 0 409 810 | 1/1991 | |
| EP | 455 929 A1 | 1/1991 | |
| EP | 606 566 A1 | 7/1994 | |
| FR | 2 289 160 | 10/1974 | |
| FR | 2 421 595 | 3/1979 | |
| GB | 834256 | 5/1960 | |
| GB | 2045083 A | 1/1984 | |
| GB | 2252501 A | 8/1992 | |
| JP | 1148254 | 6/1989 | ...................... 623/16 |
| SE | 332 486 | 11/1971 | |
| WO | WO 92/05745 | 4/1992 | |
| WO | WO 94/13334 A | 6/1994 | |

OTHER PUBLICATIONS

Curtis, A. S. G., et al., "*The Effects of Topographic and Mechanical Properties of Materials on Cell Behavior,*" Critical Reviews in Biocompatibility, vol. 5, Issue 4, pp. 343-362 (1990).

de Groot, K., et al., "*Plasma Sprayed Coatings of Hydroxylapatite,*" Journal of Biomedical Materials Research, vol. 21, pp. 1375-1381 (1987).

Gotfredsen, K., et al., "Histomorphometric and Removal Torque Analysis for $TiO_2$-Blasted Titanium Implants" Clinical Oral Impl. Res., Feb. 6, 1992, pp. 77-84.

Kasemo, B., et al., "*Metal Selection and Surface Characteristics,*" Tissue-Integrated Prostheses Osseointegration in Clinical Dentistry (Quintessence Books), pp. 99-116 (1985).

Klokkevold, P., et al., "*Evaluation of a New Chemically Enhanced Implant Surface by Torque Removal Tests in the Rabbit Femur,*" Clinical Oral Implants Research (1997).

Lazzara, R., et al., "*Retrospective Multicenter Analysis of 31 Endosseous Dental Implants Placed Over a Five Year Period,*" Clinical Oral Implants Research, vol. 7, pp. 73-83 (1996).

Messersmith, P., et al., "*Stress Enhancement and Fatigue Susceptibility of Porous Coated Ti-6Al-4V Implants: An Elastic Analysis,*" Journal of Biomedical Materials Research, vol. 24, pp. 591-604 (1990).

Olefjord, Ingemar, et al., "*Surface Analysis of Four Dental Implant Systems,*" International Journal of Oral & Maxillofacial Implants, vol. 8, No. 1, pp. 32-40 (1993).

Predecki, Paul, et al., "*Attachment of Bone to Threaded Implants by Ingrowth and Mechanical Interlocking,*" Journal of Biomedical Materials Research, vol. 6, pp. 401-412 (1972).

Schulte, J., "*External Hex Manufacturing Tolerances of Six Implant Systems: A Pilot Study,*" Implant Dentistry, pp. 51-53 (Spring 1994).

Sorensen, J., et al., "*Comparison of Interface Fidelity of Implant Systems,*" Journal of Dental Research, vol. 70, No. 540, Abstract No. 2191 (1991).
Sullivan, Daniel, et al., "*Preliminary Results of a Multicenter Study Evaluating Chemically-Enhanced Pure Titanium Implants,*" Journal of Prosthetic Dentistry (1997).
Thomas, K. A., et al., "*The Effect of Surface Macrotexture and Hydroxylapatite Coating on the Mechanical Strengths and Histologic Profiles of Titanium Implant Materials,*" Journal of Biomedical Materials Research, vol. 21, pp. 1395-1414 (1987).
University of Bern (Switzerland), Clinic for Dental Maintenance (Schweizerisch Monatschrift für Zahnheilkunde, vol. 86, No. 7, Jul. 1976, pp. 713-727).
Weinlaender, M., et al., "*Histomorphometry of Bone Apposition Around Three Types of Endosseous Dental Implants,*" International Journal of Oral & Maxillofacial Implants, vol. 7, No. 4, pp. 491-496 (1992).
Wheeler, Stephen L., "*Eight Year Clinical Retrospective Study of Titanium Plasma-Sprayed and Hydroxyapatite-Coated Cylinder Implants,*" International Journal of Oral & Maxillofacial Implants, vol. 11, No. 3, pp. 340-350 (1996).
Wong, M., et al., "*Effect of Surface Topology on the Osseointegration of Implant Materials in Trabecular Bone,*" Journal of Biomedical Materials Research, vol. 29, pp. 1567-1575 (1995).
Yue, S., et al., "*The Fatigue Strength of Porous-Coated Ti-6%Al-4%V Implant Alloy,*" Journal of Biomedical Materials Research, vol. 18, pp. 1043-1058 (1984).
Albrektsson, T., et al., "Osseointegrated Titanium Implants" (1991).
Baier, R. E., et al., "Implant Surface Preparation," *International Journal of Oral & Maxillofacial Implants*, vol. 3, pp. 9-20 (1988).
Baier, R. E., et al., "Surface Energetics and Biological Adhesion," *International Symposium on Physicochemical Aspects of Polymer Surfaces*, vol. 2, pp. 895-909 (no date).
Binon, P., "Evaluation of Machining Accuracy and Consistency of Selected Implants, Standard Abutments, And Laboratory Analogs," *International Journal of Prosthodontics*, vol. 8, pp. 162-178 (1995).
Bowers, K., et al., "Optimization of Surface Micromorphology for Enhanced Osteoblast Responses In Vitro," *International Journal of Oral & Maxillofacial Implants*, vol. 7, No. 3, pp. 302-310 (1992).
Buser, D., et al., "Influence of Surface Characteristics on Bone Integration of Titanium Implants, A Histomorphometric Study in Miniature Pigs," *Journal of Biomedical Materials Research*, vol. 25, pp. 889-902 (1991).
Carlsson L., et al., "Removal Torques for Polished and Rough Titanium Implants," *International Journal of Oral & Maxillofacial Implants*, vol. 3, pp. 21-24 (1988).
Cook, S., et al., "Fatigue Properties of Carbon- and Porous-Coated Ti-6Al-4V Alloy," *Journal of Biomedical Materials Research*, vol. 18, pp. 497-512 (1984).
Eberhardt, A., et al., "Effects of Precoating Surface Treatments on Fatigue of Ti-6Al-4V," *Journal of Applied Biomaterials*, vol. 6, pp. 171-174 (1995).
Ingemar, Olefjord, et al., "Surface Analysis of Four Dental Implant Systems," *International Journal of Oral & Maxillofacial Implants*, vol. 8, No. 1, pp. 32-40 (1993).
Ledermann et al., "The Ha-TI Implant," *Schweiz Monatsschr Zahnmed*, vol. 101, No. 5, 7 pages (May 1991).
Shultz, R. R., et al., "A Study of Fatigue Properties of Hydroxylapatite Coated Titanium Alloy Implant Materials," *Department of Biomedical Engineering, Memphis State University* (no date).
Sutter et al., "The New Restorative Concept of the ITI Dental Implant System: Design and Engineering," vol. 13, No. 5, pp. 408-413 (1993).
Tarnow, Dennis P., DDS, "Dental Implants in Periodontal Care," *Current Science*, pp. 157-162 (1993).
Wennerberg, A., et al., "Design and Surface Characteristics of 13 Commercially Available Oral Implant Systems," *International Journal of Oral & Maxillofacial Implants*, vol. 8, No. 6, pp. 622-633 (1993).
Wilke, H. J., et al., "The Influence of Various Titanium Surfaces on the Interface Shear Strength Between Implants and Bone," *Advances in Biomaterials*, Elsevier Science Publishers B.V., Amsterdam, vol. 9, pp. 309-314 (1990).
"Ion-Beam-Sputter Modification of the Surface Morphology of Biological Implants," *J. Vac. Soc. Technol.*, vol. 14, No. 1, pp. 326-331 (Jan./Feb. 1977).
"Short-Term Plasma-Cleaning Treatments Enhance In Vitro Osteoblast Attachment to Titanium," *Journal of Oral Implantology*, vol. XVIII, No. 2, pp. 130-137 (1992).
"Step-Screw Implant," *Dental Products Report* (Mar. 1993).
Schulte, W., et al., "The First 15 Years of the Tuebinger Implant and its Further Development to the Frialit®-2 System," Zeitschrift für Zahnärztliche Implantologie, Band VIII, cover page, pp. 3-22 (Feb. 1992).
Product Literature for Frialit®-2 Implant System, Interpore International and Friatec, 3 pages (1996).
Gomez-Roman, German, et al., "The Frialit-2 Implant System: Five-Year Clinical Experience in Single-Tooth and Immediately Postextraction Applications," The International Journal of Oral & Maxillofacial Implants, vol. 12, No. 3, pp. 299-309 (1997).
Product Literature for Frialit®-2, Abridged Directions for Use, Interpore International and Friatec, 20 pages (believed to be 1996 or 1997).
"The Influence of Implant Surface on Hard- and Soft Tissue Integration," Friatec website, 11 pages (written after Jun. 6, 1998).
Price List, Friatec, 40 pages (Oct. 1998).
Product Literature for Frialit®-2 Implant System, Friadent, 12 pages (Feb. 1999).
Price List and Catalog, Friadent, 35 pages (Sep. 2000).
Product Literature for Frialit®-2, Friadent, 2 pages (believed to be 2000).
Daniel Buser, DDS, et al., "Removal Torque Values of Titanium Implants in the Maxilla of Miniature Pigs", pp. 611-619.
David E. Steflik, MS, EdD, et al., "Histomorphometry of the Dental Implant-Bone Interface: One-Year Results of a Comparative Invesitgation in Dogs", pp. 501-511.
David E. Steflik, MS, EdD, et al., "A Comparative Investigation in Dogs: 2-Year Morphometric Results of the Dental Implant-Bone Interface", pp. 15-25.
Paragon Technology Report (Oct. 1997).
Bio Materials 1996 vol. 17, No. 6 pp. 605-616 "Bone response to surface-modified titanium implants: studies on the early tissue response to machined and electropolished implants with different oxide thicknesses", Larsson et al.
Bio Materials 1994 vol. 15, No. 13, pp. 1062-1074 "Bone response to surface modified titanium implants: studies on electropolished implants with different oxide thicknesses and morphology", Larsson et al.
Journal of Materials Science Materials in Medicine (1997), pp. 721-729 "Bone response to surface modified titanium implants—studies on the tissue response after 1 year to machined and electropolished implants with different oxide thicknesses".
Strauman SLA: Reducing healing time further.
Strauman Literature Abstracts.
Standard Practice for Surface Preparation and Marking of Metallic Surgical Implants (Ref. D5).
Standard Recommended Practice for Descaling and Cleaning Titanium and Titanium Alloy Surfaces (Ref. D6).
W. Eugene Roberts, D.C.S., Ph.D., et al., "Osseous adaptation to continuous loading of rigid endosseous implants" (Ref. D7).
W. M. Murphy, "Tissue Reaction of Rats and Guinea-Pigs to Co-Cr Implants With Different Surface Finishes" (Ref. D8).
Patrick J. Henry, B.D.Sc., M.S.D., F.R.A.C.D.S., "Comparative Surface Analysis of Two Osseointegrated Implant Systems" (Ref. D19).
Clinical Implant Materials, G. Heimke et al. "The Influence of Various Titanium Surfaces on the Interface Shear Strength Between Implants and Bone" (Ref. D21).
Ann Wennerberg DDS et al., "Design and Surface Characteristics of 13 Commercially Available Oral Implant Systems" (Ref. 24).
Adhesion of Bone to Titanium (Ref. 27), (1986).
Todd Smith "The Effect of Plasma-Sprayed Coatings on the Fatigue of Titanium Alloy Implants" (Ref. 29), (1994).
The Dependence of the Removal Torque of a Leg Screw Surface and Implantation Time (Ref. D30), (1976).
Implant Matrials in Biofunction, C. de Putter et al., "Removal Forces for Osseointegrated Titanium Implants" (Ref. 31), (1988).

Denar Introduces Steri-Oss: The First Complete Oral Rehabilitation Implant System.

An animal study of c.p. titanium screws with different surface topographies (Ref. D 32), (1995).

A histomorphometric and removal torque study of screw-shaped titanium implants with three different surface topographies (Ref. D33).

S.A.V. Swanson, DSc (Eng), PhD, DIC, ACGI, MIMechE, et al. "The Scientific Basis of Joint Replacement" (Ref. D41), (1977).

Dana C. Mears, B.M., B.Ch., Ph.D., M.R.C.P., F.R.C.S. (C), "Materials and Orthopaedic Surgery" (Ref 42), (1979).

Per-Ingvar Branemark, M.D., Ph.D., "Tissue-Integrated Prostheses" (Ref. 43), (1985) p. 137.

Kevin A. Thomas et al., "An evaluation of variables influencing implant fixation by direct bone appostion" (Ref. 46), (1985).

Stephen D. Cook, Ph.D. et al., "Interface Mechanics and Histology of Titanium and Hydroxylapatite-Coated Titanium for Dental Implant Applications" (Ref. 47).

Effect of a Blycoprotein Monomolecular Layer on the Integration of Titanium Implants in Bone (Ref. D48).

Removal Torques for Polished and Rough Titanium Implants (Ref. D49).

"The Influence of Various Titanium Surfaces on the Interface Shear Strength Between Implants and Bone," *Clinical Implant Materials*, edited by G. Heimke, U.Soltesz and A.J.C. Lee, *Advances in Biomaterials*, vol. 9, 1990 pp. 309-314.

Buser et al., "Influence of Surface Characteristics on Bone Integration of Titanium Implants. A Histomorphometric Study in Miniature Pigs," *Journal of Biomedical Materials Research*, vol. 25, 889-902 (1991), pp. 889-902.

Martin et al., "Effect of Titanium Surface Roughness on Proliferation, Differentiation, and Protein Synthesis of Human Osteoblast-Like Cells (MG63)," *Journal of Biomedical Materials Research*, vol. 29, 389-401 (1995), pp. 389-402.

Schwartz et al., "Effect of Titanium Surface Roughness on Chonrocyte Proliferation, Matrix Production, and Differentiation Depends on the State of Cell Maturation," *Journal of Biomedical Materials Research*, vol. 30, 145-155 (1996), pp. 145-155.

Cochran et al., "Evaluation of an Endosseous Titanium Implant With a Sandblasted and Acid-Etched Surface in the Canine Mandible: Radiographic Results," *Clinical Oral Implants Research* 1996: 7: 240-252.

Kiesweiter et al., "Surface Roughness Modulates the Local Production of Growth Factors and Cytokines by Osteoblast-Like MG-63 Cells," *Journal of Biomedical Materials Research*, vol. 32, (1996), pp. 55-63.

Cochran et al., "Bone Response to Unloaded and Loaded Titanium Implants With a Sandblasted and Acid-Etched Surface: A Histometric Study in the Canine Mandible," *J Biomed Mater Res*, 40 (1998), pp. 1-11.

Boyan et al., "Titanium Surface Roughness Alters Responsiveness of MG63 Osteoblast-Like Cells to $1\alpha,25\text{-(OH)}_2D_3$," *J Miomed Mater Res*, 39 (1998), pp. 77-85.

Buser et al., "Interface Shear Strength of Titanium Implants With a Sandblasted and Acid-Etched Surface: A Biomechanical Study in the Maxilla of Miniature Pigs," *J Biomed Mater Res*, 45 (1999), pp. 75-83.

Persson LG, Berglundh T, Sennerby L, Lindhe J., "Re-Osseointegration After Treatment of Peri-Implantitis at Different Implant Surfaces. An Experimental Study in the Dog," *Clin Oral Impl. Res.*, 12 (2001), pp. 595-603.

Karagianes, M. T., D.V.M., "*Porous Metals As a Hard Tissue Substitute*," Biomat. Med. Dev., Art. Org., vol. 1, No. 1, pp. 171-181 (1973).

Wheeler, K. R., et al., "*Porous Metals As a Hard Tissue Substitute. Part II. Porous Metal Properties*," Biomat. Med. Dev., Art. Org., vol. 1, No. 2, pp. 337-348 (1973).

Wood, William G. II, American Society for Metals Handbook "Surface Cleaning Finishing, and Coating", $9^{th}$ ed. vol. 5.

Translation of Japanese Patent JP3146679A2 published Jun. 21, 1991.

Declaration of Prabhu Gubbi presenting information on the surfaces of 61 implants (Nov. 2, 2001).

"Design and Surface Characteristics of 13 Commercially Available Oral Implant Systems," *Int. J. Oral Maxillofactial Implants*, 1993, 8:622-633, by Wennerberg et al.

"Influence of Surface Characteristics on Bone Integration of Titanium Implants," *Journal of Biomedical Materials Research*, vol. 25, pp. 889-902, John Wiley & Sons, Inc., 1991, by Buser et al.

\* cited by examiner

INFECTION-BLOCKING DENTAL IMPLANT

CROSS REFERENCES TO RELATED APPLICATIONS

This application is a continuation of U.S. application Ser. No. 08/778,503, filed Jan. 3, 1997, now issued as U.S. Pat. No. 5,863,201, which is a complete application claiming the benefit of U.S. Provisional Application No. 60/009,592, filed Jan. 4, 1996, and which is also a continuation-in-part of U.S. application Ser. No. 08/607,903, filed Feb. 27, 1996, now issued as U.S. Pat. No. 5,876,453, which, in turn, claims priority to PCT/US95/15576 and is a continuation-in-part of U.S. application Ser. No. 08/351,214, filed Nov. 30, 1994, now abandoned the parent of U.S. application Ser. No. 08/650,594, now issued as U.S. Pat. No. 5,603,338.

FIELD OF THE INVENTION

This invention relates to dental implants intended for insertion in a hole provided in living jawbone for eventual support of artificial teeth. It is illustrated as realized in a cylindrical dental implant having a screw thread or screw threads on its outer surface, but it is not limited to that type of implant, and is applicable to all types of implants which share the general characteristic that while they are fitted into the living jawbone they extend out of it through the overlying gingival into the mouth wherein they support artificial teeth.

BACKGROUND OF THE INVENTION

The part of a dental implant that is in the living jawbone should have a roughened surface confronting the host bone for bonding with the bone, and the part of the same implant that is exposed in the mouth should have a smooth surface because a rough surface in that location might provide a site where bacteria can attach and proliferate. For hygienic reasons the exposed surfaces of the implant should be smooth, while for osseointegration purposes the surfaces of the implant confronting the host bone should be rough. Experience over many years has taught dentists practicing implantology that approximately eighteen months after an implant has been successfully placed in the jawbone of a patient and is performing its task of supporting artificial dentition, the bone surrounding the implant immediately beneath the overlying gingival tissue will in most cases be found to have receded a small distance, exposing to the soft tissue a portion of the roughened surface of the implant which had been in bone. This phenomenon is illustrated in a book by Branemark, Zarb & Albrektsson entitled "Tissue-Integrated Prostheses" 1985, p56, FIG. 1-46. This event, occurring as it does beneath the gum tissue surrounding an artificial tooth, is not immediately visible. In spite of the most diligent hygienic practice, it presents the danger that bacteria which succeed in penetrating between the tooth and its surrounding tissue may attach themselves to the roughened surface, and there proliferate, and bring about an infection putting the implant and the tooth it supports in danger of failure.

In U.S. Pat. No. 4,988,299 an implant is disclosed which has a threaded portion and a smooth neck portion. No reference is made to roughening of the threaded portion or how smooth the neck portion should be. The neck portion is defined by having a diameter between the "core" diameter of the threaded portion and the outer diameter of the threads and it is disclosed to have a curved surface. The neck portion is said to have an axial length exceeding the settlement in bone level and it is intended to avoid exposure of the threads.

SUMMARY OF THE INVENTION

The present invention relates to an implant which is roughened to improve osseointegration with the bone but which does not provide a surface which can facilitate infection.

Observations based on practical experience of one of the present inventors over the past ten years or more have revealed that the recession described in the above-mentioned book tends to stop at the level where the implant places a load on the host bone. In a screw-type implant this level is approximately the beginning of the first turn of the screw thread near the gingival end of the implant. However, these observations also indicate that the stopping level is not precisely the same in all cases, and that in some cases the first thread may be exposed. At times, more than one thread is exposed, perhaps up to three threads.

According to the invention as illustrated in the accompanying drawings, the portion of the implant which has a roughened surface is limited to that portion which can be expected to remain in contact with the host bone after the expected bone recession has taken place. The head portion of the implant and the immediately-adjacent part of the heretofore roughened portion, including the initial part of the screw threads, are made smooth. Preferably one to three threads will be left smooth, not roughened. Typically, a length of about 3 mm below the top surface of the implant will be left smooth and not roughened with the remainder of the implant. Because the amount of bone that recedes will vary with different patients, one or more smooth threads may remain permanently in the bone along with the roughened threads. Although these smooth threads may not load the bone to the same degree as the roughened threads, nevertheless the smooth threads will still add significantly to the bone loading.

Since the exact amount of bone recession that will occur in a given patient cannot be determined in advance of the event with precision, the invention is useful to minimize the danger of infection from this source, that is, to block the infection. Good hygienic practice will continue to be required of the patient. With the invention, such good practice can be expected to be more fruitful than heretofore.

BRIEF DESCRIPTION OF THE DRAWINGS

The invention is described in greater detail with reference to the accompanying drawings, in which.

DETAILED DESCRIPTION OF THE INVENTION

Figure 1:
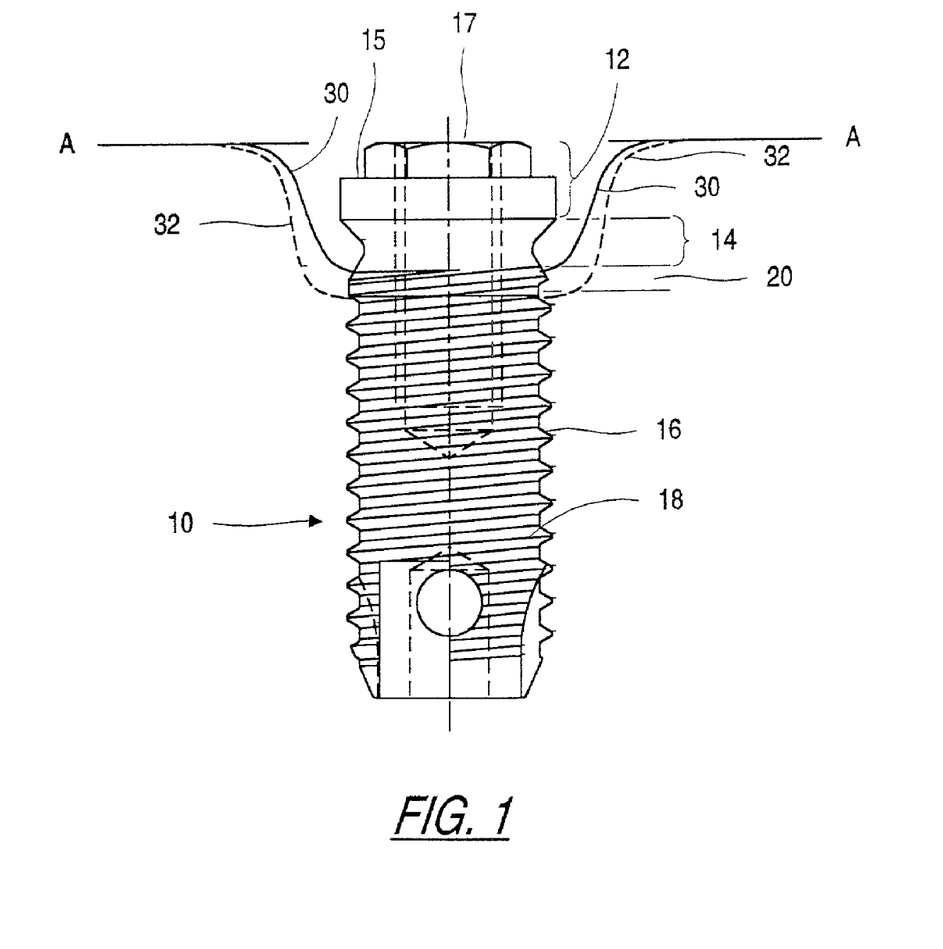
FIG. 1 is a side elevation of a dental implant according to the invention.
Figure 2:
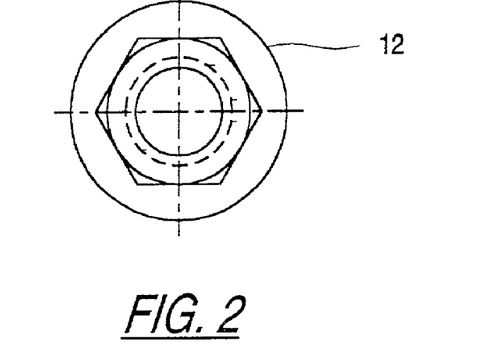
FIG. 2 is an end view of the dental implant of FIG. 1.
Figure 3A:
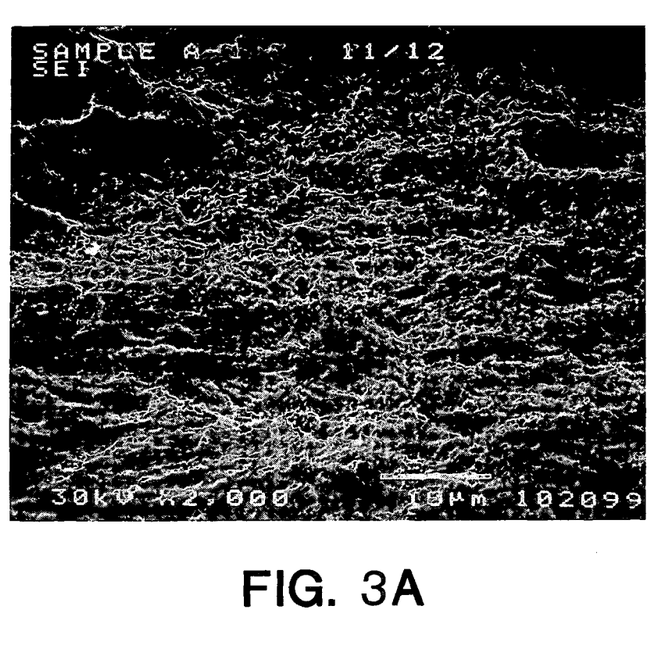
FIGS. 3A and 3B are scanning electron micrographs ("SEMs") of two titanium dental implants prepared in accordance with the present invention.
Figure 3B:
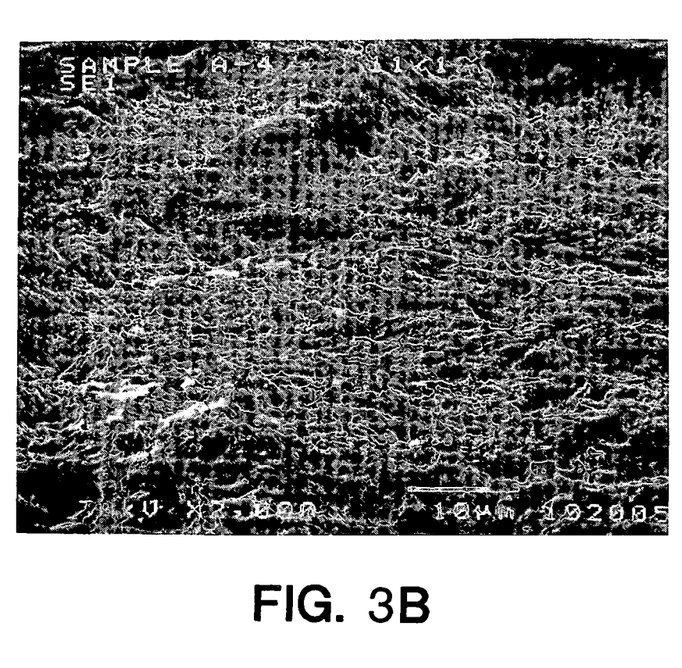
Figure 4A:
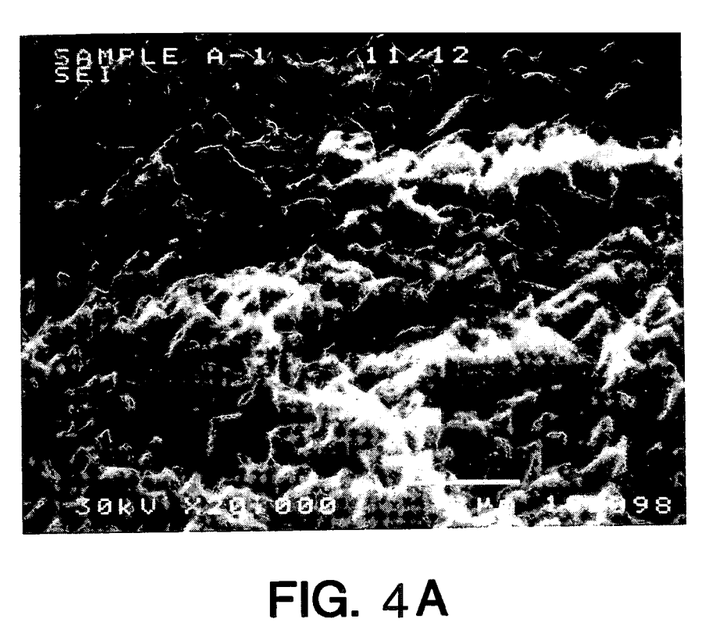
FIGS. 4A and 4B are SEMs of the same implants shown in FIGS. 3A and 3B, at a higher magnification level.
Figure 4B:
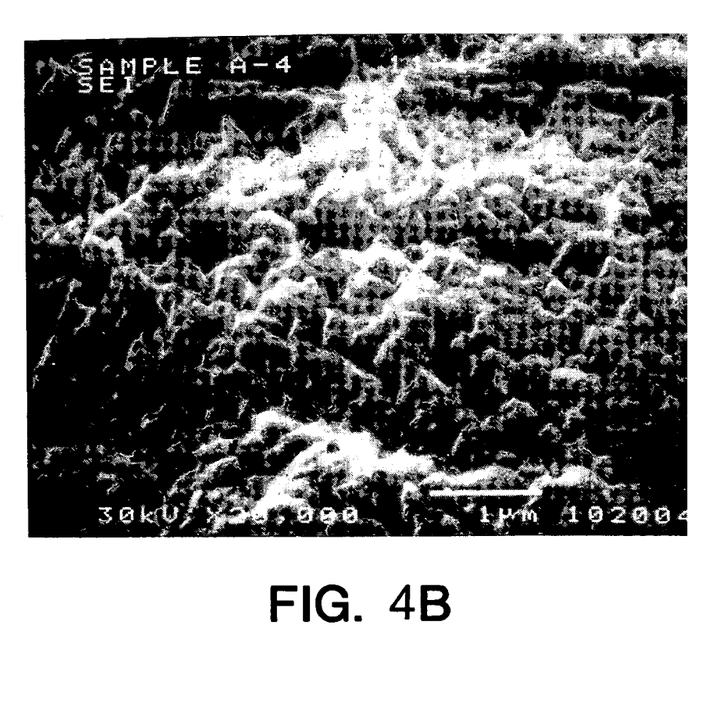
Figure 5:
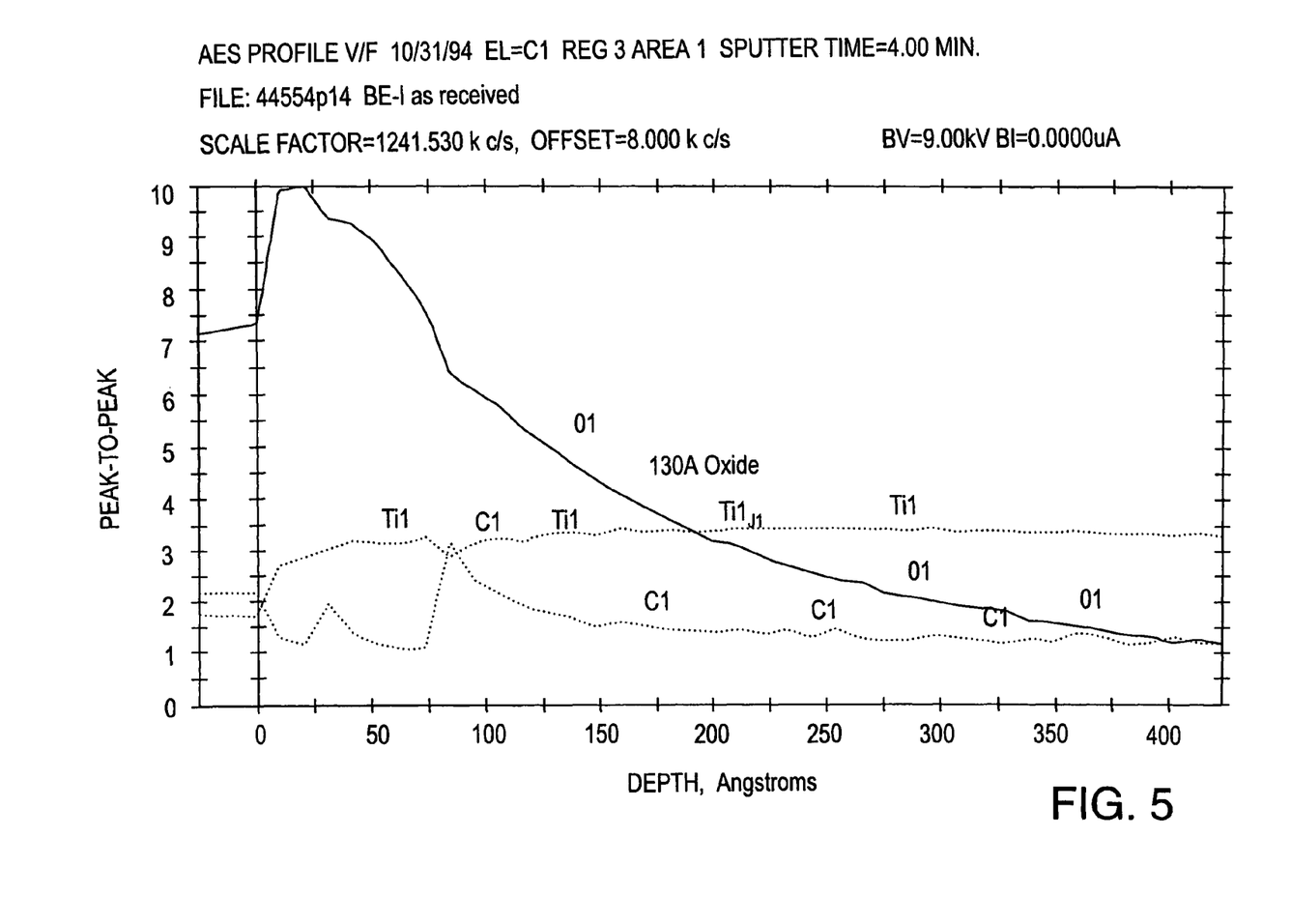
FIG. 5 is a graph of the results of an Auger electron spectroscopic analysis of a titanium surface that has been exposed to air.
Figure 6A:
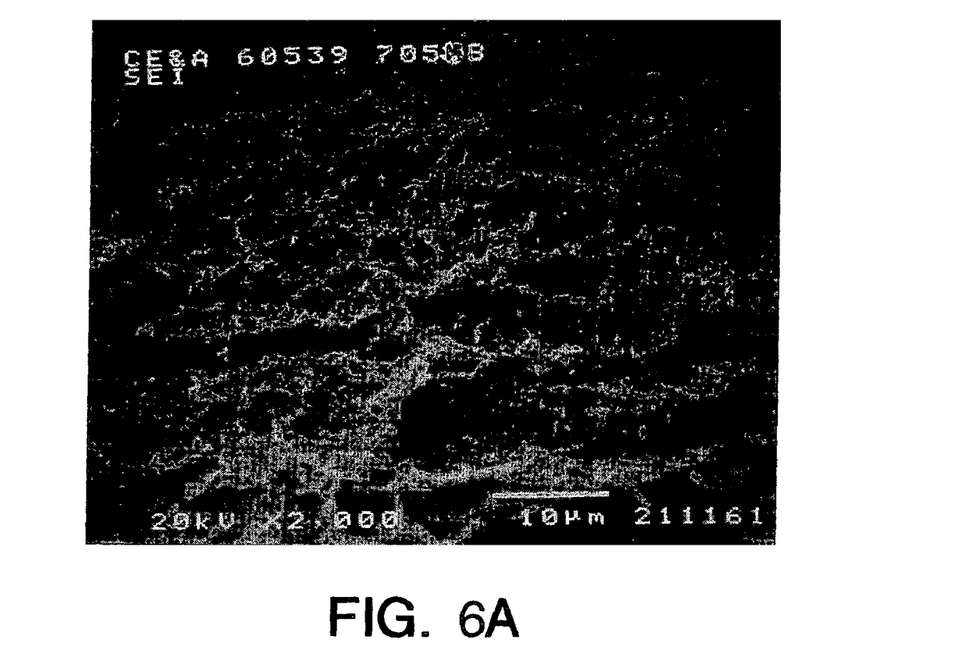
FIGS. 6A and 6B are SEMs of two titanium dental implants prepared in accordance with the present invention.
Figure 6B:
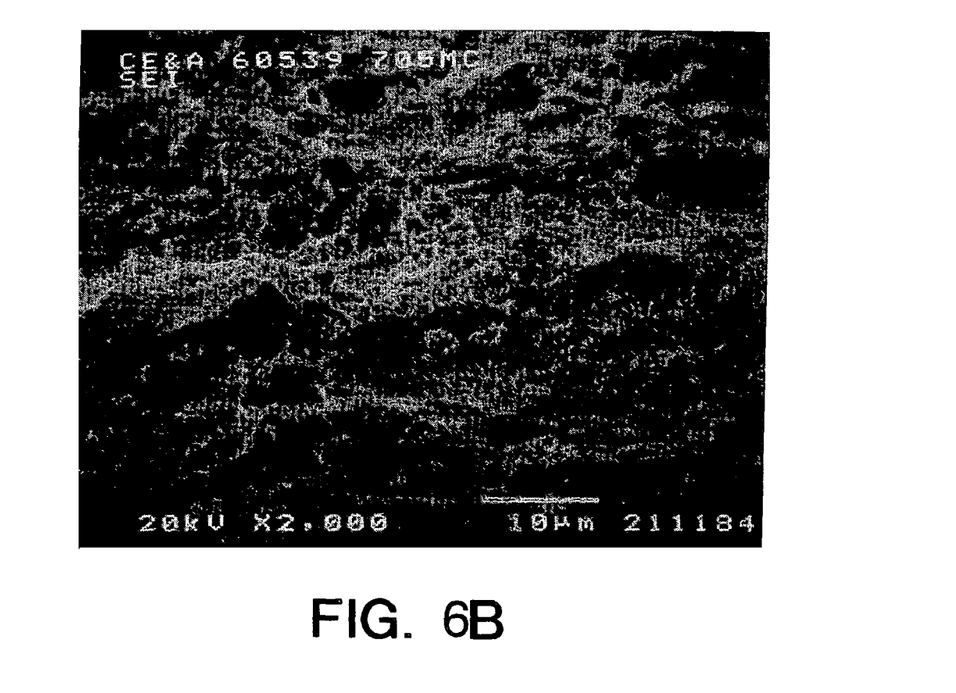
Figure 7A:
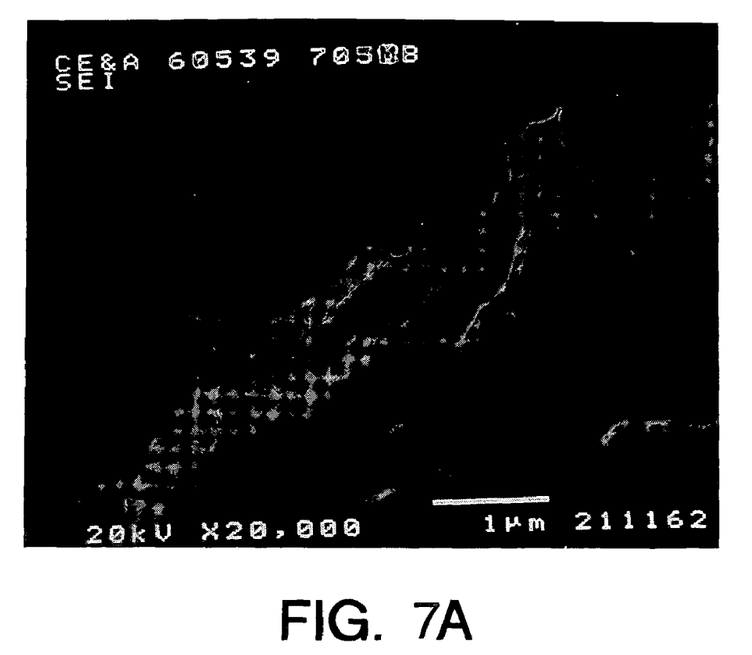
FIGS. 7A and 7B are SEMs of the same implants shown in FIGS. 7A and 7B, at a higher magnification level.
Figure 7B:
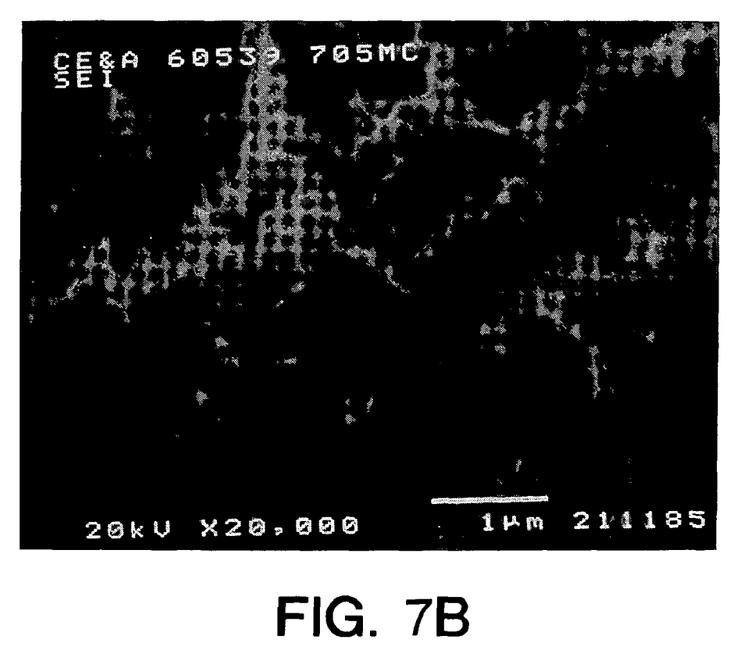

The implant 10 has a head portion 12, a neck portion 14 and a main body 16 which is roughened on its outer surface in the region 18. Such implants are normally machined from titanium or a titanium alloy and are smooth, until a portion is roughened to facilitate osseointegration with bone. The head portion 12, the neck portion 14, and a small region 20 of the main body 16 immediately adjacent the neck portion, encompassing the first to third thread turns, are smooth. To achieve this result the portions of the implant intended to remain smooth during and after the roughening procedure may be covered during that procedure. For example, if the roughening procedure includes an acid-etching step or steps, these parts may be covered with a suitable wax prior to immersing the implant in the etching acid. A preferred method of roughening the surface is disclosed in U.S. Pat. No. 5,876,453 mentioned above and incorporated by reference herein. The process has two steps, the first being removal of native oxide from titanium by contact with an aqueous hydrofluoric acid solution, followed by etching with a mixture of sulfuric and hydrochloric acids.

When the implant 10 is first installed in a bore prepared for it in a patient's jawbone, the implant is buried in bone up to and including the head portion 12, to the level indicated by line A-A in FIG. 1. The healing phase then begins, during which new bone is formed close to the immobile, resting implant, and the implant will remain buried in the bone, up to the head portion. All the implant, including the neck portion 12, will confront the host bone in the early part of the healing phase. Thereafter when the implant is loaded and the remodeling phase begins (overlapping the healing phase) during exposure to masticatory forces, the newly formed bone remodels under the applied load until, after about eighteen months, a steady state is achieved. In this state the anchoring bone will be found to have undergone a reduction in height (bone recession) immediately adjacent the implant. The amount of this recession can vary from case to case, between the level indicated by the solid curved lines 30 and the level indicated by the broken curved lines 32, for example, exposing the head portion 12, the neck portion 14 and some or all of the immediately adjacent region 20 of the threaded main body 16. In some cases region 20 may extend further, up to about the third thread. Another way to define regions 14 and 20 is that roughening of the implant begins about 3 mm below the upper flat surface 15 of the implant 10, which receives connecting parts of the dental restoration.

According to the invention, that region 20 immediately adjacent to the neck portion 14 of the implant is maintained smooth so that when the remodeling phase is completed, there will be little or no roughened implant surface exposed to the soft tissue under the dental restoration that is supported on the implant. The exact dimensions of the smooth region 20 cannot be precisely established for all cases. A length corresponding to about one turn of the screw thread is suitable for many cases, but up to three threads may be left smooth.

The manner in which the surface of the implant is roughened and the resulting surface topography will now be described. According to one aspect of the present invention, the native oxide layer is removed from the surface of a titanium implant prior to the final treatment of the surface to achieve the desired topography. After the native oxide layer is removed, a further and different treatment of the surface is carried out in the absence of unreacted oxygen to prevent the oxide layer from reforming until after the desired surface topography has been achieved. It has been found that this process permits the production of unique surface conditions that are substantially uniform over the implant surface that is so treated.

Removal of the native oxide layer can be effected by immersing the titanium implant in an aqueous solution of hydrofluoric (HF) acid at room temperature to etch the native oxide at a rate of at least about 100 Angstroms per minute. A preferred concentration for the hydrofluoric acid used in this oxide removal step is 15% $HF/H_2O$. This concentration produces an etch rate of approximately 200-350 Angstroms per minute at room temperature, without agitation, so that a typical native oxide layer having a thickness in the range from about 70 to about 150 Angstroms can be removed in about one-half minute. Other suitable etching solutions for removing the native oxide layer, and their respective etch rates, are:

50% HF—etch rate about 600 to 750 Angstroms/min.
30% HF—etch rate about 400 to 550 Angstroms/min.
10% HF—etch rate about 100 to 250 Angstroms/min.

A 100% HF was found to be difficult to control, and the etch rate was not determined. The preferred 15% HF solution allows substantially complete removal of the native oxide layer with minimum further consumption of the titanium surface after the implant is removed from the solution.

The native oxide layer may be removed by the use of other acids, or by the use of techniques other than acid etching. For example, the Swart et al. article cited above mentions the use of plasma cleaning to remove thin oxides. Regardless of what technique is used, however, it is important to remove substantially all the native oxide from the implant surface that is intended to interface with the living bone, so that the subsequent treatment of that surface produces a substantially uniform surface texture to promote uniform bonding to the living bone. The native oxide layer is preferably removed from substantially the entire bone-interfacing surface of the implant. In the case of screw-type dental implants, the bone-interfacing surface typically includes the entire implant surface beyond a narrow collar region on the side wall of the implant at the gingival end thereof. This narrow collar region preferably includes the first turn of the threaded portion of the implant. It is preferred not to etch the gingival end itself, as well as the narrow collar region, because these portions of the implant are normally fabricated with precise dimensions to match abutting components which are eventually attached to the gingival end of the implant. Moreover, it is preferred to have a smooth surface on that portion of a dental implant that is not embedded in the bone, to minimize the risk of infection.

The treatment that follows removal of the native oxide layer must be different from the treatment that is used to remove the native oxide layer. A relatively aggressive treatment is normally required to remove the oxide layer, and such an aggressive treatment does not produce the desired uniform surface texture in the resulting oxide-free surface. Thus, after the native oxide layer has been removed, the resulting implant surface is immediately rinsed and neutralized to prevent any further attack on the implant surface. The surface is then subjected to the further, and different, treatment to produce a desired uniform, surface texture. For example, the preferred further treatment described below is a relatively mild acid-etching treatment which forms a multitude of fine cone-like structures having relatively uniform, small dimensions. Because of the prior removal of the native oxide layer, even a mild second treatment of the implant surface can produce a substantially uniform effect over substantially the entire bone-interfacing surface of the implant.

Prior to removing the native oxide layer, the oxide-bearing surface may be grit blasted, preferably with grit made of titanium or a dilute titanium alloy. As is taught in the U.S. Patent No. 5,607,480, the use of a grit made of titanium avoids contaminating the surface of a titanium implant. Thus, for a dental implant made of commercially pure ("CP") titanium, the blasting material may be CP B299 SL grade titanium grit.

The preferred particle size for this grit is in the range from about 10 to about 60 microns (sifted), and the preferred pressure is in the range from about 50 to about 80 psi.

The surface treatment that follows removal of the native oxide layer from the implant surface may take several forms, singly or in combination. The preferred treatment is a second acid etching step, using an etch solution ("Modified Muriaticetch") consisting of a mixture of two parts by volume sulfuric acid (96% by weight $H_2SO_4$, 4% by weight water) and one part by volume hydrochloric acid (37% by weight HCl, 63% by weight water) at a temperature substantially above room temperature and substantially below the boiling point of the solution, preferably in the range from about 60° C. to about 80° C. This mixture provides a sulfuric acid/hydrochloric acid ratio of about 6:1. This preferred etch solution is controllable, allowing the use of bulk etch times in the range from about 3 to about 10 minutes. This solution also can be prepared without the risk of violent reactions that may result from mixing more concentrated HCl solutions (e.g., 98%) with sulfuric acid. This second etching treatment is preferably carried out in the absence of unreacted oxygen, and before the implant surface has been allowed to re-oxidize, following removal of the native oxide layer. Of course, the implants may be kept in an inert atmosphere or other inert environment between the two etching steps.

The second etching step produces a surface topography that includes many fine projections having a cone-like aspect in the sub-micron size range. Because of the fine roughness of the surface, and the high degree of uniformity of that roughness over the treated surface, the surface topography produced by this process is well suited for osseointegration with adjacent bone. As illustrated by the working examples described below, the final etched surface consists of a substantially uniform array of irregularities having peak-to-valley heights of less than about 10 microns. Substantial numbers of the irregularities are substantially cone-shaped elements having base-to-peak heights in the range from about 0.3 microns to about 1.5 microns. The bases of these cone-shaped elements are substantially round with diameters in the range from about 0.3 microns to about 1.2 microns, and spaced from each other by about 0.3 microns to about 0.75 microns. The SEMs discussed below, and reproduced in the drawings, illustrate the surface topography in more detail.

The acid-etched surface described above also provides a good site for the application of various materials that can promote bonding of the surface to adjacent bone. Examples of such materials are bone-growth-enhancing materials such as bone minerals, bone morphogenic proteins, hydroxyapatite, whitlockite, and medicaments. These materials are preferably applied to the etched surface in the form of fine particles which become entrapped on and between the small cone-like structures. The bone-growth-enhancing materials are preferably applied in the absence of oxygen, e.g., using an inert atmosphere.

The roughness of the surface to which these materials are applied enhances the adherence of the applied material to the titanium implant. The uniformity of the rough surface enhances the uniformity of the distribution of the applied material, particularly when the material is applied as small discrete particles or as a very thin film.

A preferred natural bone mineral material for application to the etched surface is the mineral that is commercially available under the registered trademark "BIO-OSS". This material is a natural bone mineral obtained from bovine bone; it is described as chemically comparable to mineralized human bone with a fine, crystalline biological structure, and able to support osseomtegration of titanium fixtures.

The invention will be further understood by reference to the following examples, which are intended to be illustrative and not limiting:

EXAMPLE NO. 1

A batch of 30 screw-type cylindrical implants made of CP titanium were grit blasted using particles of CP B299 SL grade titanium grit having particle sizes ranging from 10 to 45 microns, at a pressure of 60 to 80 psi. After grit-blasting, native oxide layer was removed from the implant surfaces by placing 4 implants in 100 ml. of a 15% solution of HF in water at room temperature for 30 seconds. The implants were then removed from the acid, neutralized in a solution of baking soda, and placed in 150 ml. of "Modified Muriaticetch" (described above) at room temperature for 3 minutes. The implants were then removed from the acid, neutralized, rinsed and cleaned. All samples displayed very similar surface topographies and a high level of etch uniformity over the surface, when compared with each other in SEM evaluations. Consistency in the surface features (peaks and valleys) was also observed. The SEMs in FIGS. 3A, 3B, 4A and 4B show the surfaces of two of the implants, Sample A-1 and Sample A-4, at magnifications of 2,000 and 20,000. It will be observed that the surface features over the areas shown are consistent and uniform. The scale shown on the ×20,000 photographs is 1 micron=0.564 inch. At this magnification the surfaces appear to be characterized by a two-dimensional array of cones ranging in height (as seen in the SEMs) from about 0.17 inch to about 0.27 inch; the base diameters of these cones varied from about 0.17 inch to about 0.33 inch. Converting these numbers to metric units on the above-mentioned scale (1 micron=0.564 inch) yields:
cone height range (approx.)=0.30 to 0.50 micron
cone base diameter range (approx.)=0.30 to 0.60 micron.

The same degree of uniformity was found in all the samples, and from sample to sample, at magnifications of 2,000 and 20,000, as compared with similar samples subjected to bulk etching without prior removal of the native oxide, as described in EXAMPLE NO. 2 below.

EXAMPLE NO. 2

Four of the implants that had been grit blasted as described in EXAMPLE NO. 1 above were placed in 150 ml. of "Modified Muriaticetch" for 10 minutes. The implants were then removed, neutralized, rinsed and cleaned. SEM photographs taken at magnifications of 2,000 and 20,000 showed that the bulk etch solution failed to remove the native oxide layer after 10 minutes in the etch solution. The failure to remove the native oxide layer (100-150 Angstrom units thick) resulted in a non-uniformly etched surface, as depicted for example in FIG. 3 of U.S. Pat. No. 5,876,453. In areas of the implant surfaces where the native oxide was removed, the topography was similar to that observed on the implants in EXAMPLE NO. 1.

EXAMPLE NO. 3

The procedure of this example is currently preferred for producing commercial implants. A batch of screw-type implants made of CP titanium were immersed in a 15% solution of HF in water at room temperature for 60 seconds to remove the native oxide layer from the implant surfaces. A plastic cap was placed over the top of each implant to protect it from the acid. The implants were then removed from the acid and rinsed in a baking soda solution for 30 seconds with gentle agitation. The implants were then placed in a second solution of baking soda for 30 seconds, again with agitation of the solution; and then the implants were rinsed in deionized water. Next the implants were immersed in another solution of two parts by volume sulfuric acid (96% by weight $H_2SO_4$, 4% by weight water), and one part by volume hydrochloric acid (37% by weight HCl, 63% by weight water) at 70° C. for 5 minutes. The implants were then removed from the acid and rinsed and neutralized by repeating the same steps carried out upon removal of the implants from the HF. All samples displayed very similar surface topographies and a high level of etch uniformity over the surface, when compared with each other in SEM evaluations. Consistency in the surface features (peaks and valleys) was also observed. The SEMs in FIGS. 6A, 6B, 7A and 7B show the surfaces of two of the implants, Sample 705MB and Sample 705MC, at magnifications of 2,000 and 20,000. It will be observed that the surface features over the areas shown are consistent and uniform. The scale shown on the ×20,000 photographs is 1 micron=0.564 inch. At this magnification the surfaces appear to be characterized by a two-dimensional array of cones ranging in height (as seen in the SEMs) from about 0.17 inch to about 1.128 inch; the base diameters of these cones varied from about 0.17 inch to about 1.128 inch. Converting these numbers to metric units on the above-mentioned scale (1 micron=0.564 inch) yields:

cone height range (approx.)=0.30 to 2.0 microns
cone base diameter range (approx.)=0.30 to 2.0 microns.

The same degree of uniformity was found in all the samples, and from sample to sample, at magnifications of 2,000 and 20,000, as compared with similar samples subjected to bulk etching without prior removal of the native oxide, as described in EXAMPLE NO. 2 above.

The invention claimed is:

1. A dental implant made of titanium metal, comprising:
   a smooth head portion for receiving a dental restoration component;
   a lowermost end opposing said head portion;
   a threaded portion for engaging bone between said head portion and said lowermost end; and
   a roughened region for facilitating osseointegration with said bone located on said threaded portion and extending to said lowermost end of said implant, said roughened region being uniformly acid etched with a second acid solution after a native oxide layer had been removed by contact with a first acid solution with minimum consumption of said titanium metal, said roughened region including an array of irregularities having peak-to-valley heights not greater than about 10 microns wherein said second acid solution is a mixture of sulfuric and hydrochloric acids.

2. A titanium metal dental implant of claim 1, wherein said first acid solution is aqueous hydrofluoric acid.

3. A titanium metal dental implant of claim 1, wherein said irregularities include cone-shaped elements.

4. A titanium dental implant, comprising:
   a head portion for receiving a dental restoration component, said head portion including a non-rotational feature for engaging said dental restoration component, said head portion having a smooth machined surface;
   a lowermost end opposing said head portion; and
   a threaded portion having continuous thread turns and being located between said head portion and said lowermost end, said threaded portion including a self-tapping region adjacent to said lowermost end, said threaded portion having an acid-etched surface for facilitating osseointegration with said bone, said acid-etched surface extending to said lowermost end of said implant and within said self-tapping region, said acid-etched surface being produced on said threaded portion after a native oxide layer has been removed from said threaded surface, said acid-etched surface having an array of irregularities having peak-to-valley heights not greater than about 10 microns, said irregularities including cone-shaped elements.

5. The implant of claim 4, said acid-etched surface is located on said threaded portion below the first uppermost turn of said threaded portion.

6. The implant of claim 4, wherein said native oxide is removed by a first acid solution after which the resulting surface is etched with a second acid solution to create said acid-etched surface.

7. The implant of claim 6, said first acid solution is aqueous hydrofluoric acid.

8. The implant of claim 7, wherein said second acid solution is a mixture of sulfuric and hydrochloric acids.

9. A titanium dental implant, comprising:
   a head portion for receiving a dental restoration component, said head portion including a non-rotational feature for engaging said dental restoration component;
   a lowermost end opposing said head portion; and
   a threaded portion having continuous thread turns and being located between said head portion and said lowermost end, said threaded portion including a cylindrical section and a tapered section immediately adjacent to said lowermost end, said cylindrical section being longer than said tapered section, said tapered section including a self-tapping region that extends to said lowermost end, said threaded portion having an acid-etched surface for facilitating osseointegration with said bone, said acid-etched surface extending from said lowermost end and into said cylindrical section of said threaded portion, said acid-etched surface being produced on said threaded portion after a native oxide layer has been removed from said threaded portion, said acid-etched surface having an array of irregularities having peak-to-valley heights not greater than about 10 microns, said irregularities including cone-shaped elements.

10. The implant of claim 9, said acid-etched surface extends from said lowermost end to at least an uppermost turn of said threaded portion.

11. The implant of claim 9, wherein said native oxide is removed by a first acid solution after which the resulting surface is etched with a second acid solution.

12. The implant of claim 11, said first acid solution is aqueous hydrofluoric acid.

13. The implant of claim 11, wherein said second acid solution is a mixture of sulfuric and hydrochloric acids.

14. The implant of claim 9, further including a neck portion between said head portion and said threaded portion.

15. The implant of claim 14, wherein said neck portion is a smooth machined surface, said head portion having a smooth machined surface.

16. The implant of claim 9, wherein said head portion has a smooth machined surface.

* * * * *